(12) United States Patent
Partain et al.

(10) Patent No.: US 11,523,623 B2
(45) Date of Patent: *Dec. 13, 2022

(54) PLANT-DERIVED PROTEIN PURIFICATION

(71) Applicant: R.J. Reynolds Tobacco Company, Winston-Salem, NC (US)

(72) Inventors: Nicholas Partain, Owensboro, KY (US); Joshua D. Morton, Evansville, IN (US); Barry Bratcher, Owensboro, KY (US); John-Paul Mua, Advance, NC (US); Kyle Ford, Germanton, NC (US)

(73) Assignee: R.J. Reynolds Tobacco Company, Winston-Salem, NC (US)

( * ) Notice: Subject to any disclaimer, the term of this patent is extended or adjusted under 35 U.S.C. 154(b) by 401 days.

This patent is subject to a terminal disclaimer.

(21) Appl. No.: 16/744,873

(22) Filed: Jan. 16, 2020

(65) Prior Publication Data

US 2020/0229461 A1 Jul. 23, 2020

Related U.S. Application Data

(60) Provisional application No. 62/794,020, filed on Jan. 18, 2019.

(51) Int. Cl.
| | | |
|---|---|---|
| *A23J 1/00* | (2006.01) |
| *A23K 20/147* | (2016.01) |
| *A23L 33/185* | (2016.01) |
| *A23J 3/14* | (2006.01) |
| *C07K 1/34* | (2006.01) |
| *C12N 9/88* | (2006.01) |

(52) U.S. Cl.
CPC .......... *A23J 1/007* (2013.01); *A23J 3/14* (2013.01); *A23K 20/147* (2016.05); *A23L 33/185* (2016.08); *C07K 1/34* (2013.01); *C12N 9/88* (2013.01); *C12Y 401/01039* (2013.01); *A23V 2002/00* (2013.01)

(58) Field of Classification Search
CPC .... A23J 1/007; A23J 3/14; A23J 1/006; A23J 1/009; A23J 3/20; A23K 20/147; A23K 10/30; A23L 33/185; A23L 5/49; C07K 1/34; C12N 9/88; C12Y 401/01039; A23V 2002/00

See application file for complete search history.

(56) References Cited

U.S. PATENT DOCUMENTS

| | | |
|---|---|---|
| 3,612,065 A | 10/1971 | Rosen |
| 3,684,520 A | 8/1972 | Bickoff et al. |
| 3,823,128 A | 7/1974 | Bickoff et al. |
| 3,943,945 A | 3/1976 | Rosen |
| 3,959,246 A | 5/1976 | Bickoff et al. |
| 4,144,895 A | 3/1979 | Fiore |
| 4,150,677 A | 4/1979 | Osborne, Jr. et al. |
| 4,267,847 A | 5/1981 | Reid |
| 4,268,632 A | 5/1981 | Wildman et al. |
| 4,289,147 A | 9/1981 | Wildman et al. |
| 4,333,871 A | 6/1982 | De Jong |
| 4,340,676 A | 7/1982 | Bourque |
| 4,347,324 A | 8/1982 | Wildman et al. |
| 4,351,346 A | 9/1982 | Brummer et al. |
| 4,359,059 A | 11/1982 | Brummer et al. |
| 4,366,823 A | 1/1983 | Rainer et al. |
| 4,366,824 A | 1/1983 | Rainer et al. |
| 4,388,933 A | 6/1983 | Rainer et al. |
| 4,400,471 A | 8/1983 | Johal |
| 4,506,682 A | 3/1985 | Muller |
| 4,588,691 A | 5/1986 | Johal |
| 4,589,428 A | 5/1986 | Keritsis |
| 4,605,016 A | 8/1986 | Soga et al. |
| 4,641,667 A | 2/1987 | Schmekel et al. |
| 4,716,120 A | 12/1987 | Tsay |
| 4,716,911 A | 1/1988 | Poulose et al. |
| 4,727,889 A | 3/1988 | Niven, Jr. et al. |
| 4,887,618 A | 12/1989 | Bernasek et al. |
| 4,941,484 A | 7/1990 | Clapp et al. |
| 4,967,771 A | 11/1990 | Fagg et al. |
| 4,986,286 A | 1/1991 | Roberts et al. |
| 5,005,593 A | 4/1991 | Fagg |
| 5,018,540 A | 5/1991 | Grubbs et al. |
| 5,060,669 A | 10/1991 | White et al. |
| 5,065,775 A | 11/1991 | Fagg |
| 5,074,319 A | 12/1991 | White et al. |

(Continued)

FOREIGN PATENT DOCUMENTS

| | | |
|---|---|---|
| JP | H08165298 | 6/1996 |
| WO | WO 94/07382 | 4/1994 |

(Continued)

OTHER PUBLICATIONS

Fu et al., "Recovery of Nicotine-Free Proteins From Tobacco Leaves Using Phosphate Buffer System Under Controlled Conditions," *Bioresource Technology*, 2010, vol. 101, pp. 2034-2042.

(Continued)

*Primary Examiner* — Paul J Holland

(74) *Attorney, Agent, or Firm* — Womble Bond Dickinson (US) LLP

(57) ABSTRACT

The disclosure describes methods for the purification of protein-enriched extracts to provide concentrates and isolates and methods for incorporation of such materials into products. The purification methods are adapted for removal of, e.g., chlorophyll and may thus provide lightening the color of the protein-enriched extracts. The methods generally include treatment with peracetic acid or hydrogen peroxide and filtrations. A protein composition in the form of a concentrate or isolate is provided, the protein composition including RuBisCO, F2 fraction proteins, or combination thereof extracted from a plant material.

19 Claims, 6 Drawing Sheets

(56) References Cited

U.S. PATENT DOCUMENTS

| | | | |
|---|---|---|---|
| 5,099,862 A | 3/1992 | White et al. |
| 5,121,757 A | 6/1992 | White et al. |
| 5,131,414 A | 7/1992 | Fagg et al. |
| 5,131,415 A | 7/1992 | Munoz et al. |
| 5,148,819 A | 9/1992 | Fagg |
| 5,197,494 A | 3/1993 | Kramer |
| 5,230,354 A | 7/1993 | Smith et al. |
| 5,234,008 A | 8/1993 | Fagg |
| 5,243,999 A | 9/1993 | Smith |
| 5,301,694 A | 4/1994 | Raymond et al. |
| 5,318,050 A | 6/1994 | Gonzalez-Parra et al. |
| 5,343,879 A | 9/1994 | Teague |
| 5,360,022 A | 11/1994 | Newton et al. |
| 5,435,325 A | 7/1995 | Clapp et al. |
| 5,445,169 A | 8/1995 | Brinkley et al. |
| 5,713,376 A | 2/1998 | Berger |
| 5,900,376 A | 5/1999 | Das et al. |
| 6,033,895 A | 3/2000 | Garger et al. |
| 6,131,584 A | 10/2000 | Lauterbach |
| 6,284,875 B1 | 9/2001 | Turpen et al. |
| 6,298,859 B1 | 10/2001 | Kierulff et al. |
| 6,772,767 B2 | 8/2004 | Mua et al. |
| 6,817,970 B2 | 11/2004 | Berit et al. |
| 6,906,172 B2 | 6/2005 | Bratcher et al. |
| 7,034,128 B2 | 4/2006 | Turpen et al. |
| 7,048,211 B2 | 5/2006 | Bratcher et al. |
| 7,337,782 B2 | 3/2008 | Thompson |
| 9,175,052 B2 | 11/2015 | Gerardi et al. |
| 9,220,295 B2 | 12/2015 | Morton et al. |
| 9,301,544 B2 | 4/2016 | Mua et al. |
| 2010/0093054 A1 | 4/2010 | Lo et al. |
| 2011/0257369 A1 | 10/2011 | Lo et al. |
| 2013/0072661 A1 | 3/2013 | Kale |
| 2014/0343254 A1 | 11/2014 | Gerardi et al. |
| 2016/0029663 A1 | 2/2016 | Gerardi et al. |

FOREIGN PATENT DOCUMENTS

| | | |
|---|---|---|
| WO | WO 96/31255 | 10/1996 |
| WO | WO 99/52537 | 10/1999 |
| WO | WO 2005/048929 | 6/2005 |
| WO | WO 2008/143914 | 11/2008 |
| WO | WO 2010/102284 | 9/2010 |
| WO | WO 2011/078671 | 6/2011 |
| WO | WO 2014/159617 | 10/2014 |
| WO | WO 2014/186671 | 11/2014 |
| WO | WO 2016/054375 | 4/2016 |
| WO | WO 2019/016762 | 1/2019 |

OTHER PUBLICATIONS

Hauck et al., "The Manufacture of Allergenic Extracts in North America," *Clinical Review in Allergy and Immunology*, 2001, pp. 93-110, vol. 21.

Curious Cook. "The New York Times" Sep. 15, 2010 [Retrieved from the Internet on: Sep. 28, 2019]. Retrieved from<URL: https://www.curiouscook.com/site/2010/09/achieving-a-distinct-flavor-without-going-to-extremes.html> (Year: 2010).

|  | Average Green Biomass over cuttings (kilograms/acre) | # Cuttings per year | Total Biomass (kg) | Average Spray Dried Rubisco (g/kg) | Total Rubisco Acre (kg) |
| --- | --- | --- | --- | --- | --- |
| Tobacco | 7666 | 3 | 22998 | 1.13 | 25.9 |
| Alfalfa | 5000 | 5 | 25000 | 2.67 | 66.8 |

FIGURE 5

PLANT-DERIVED PROTEIN PURIFICATION

FIELD

The present disclosure relates primarily to materials derived from plant sources and to methods for obtaining and purifying such materials. Purified materials provided thereby are also described herein.

BACKGROUND

Proteins are chains of amino acids that are important for the human body. Proteins are the major structural component of all cells in the body, including cells of organs, muscle, hair, and skin. Proteins provide numerous beneficial functions within the body, including helping to make new cells, repairing existing cells, and serving as an energy source for the body. Some proteins transport and store molecules (e.g., hemoglobin, which transports oxygen) and some proteins are involved in the creation of hormones that that help to control certain functions within the body. Protein deficiencies can lead to a range of symptoms such as apathy, diarrhea, inactivity, failure to grow, flaky skin, edema, etc., and can, in extreme cases, result in mental retardation or death.

To provide the range of necessary functions referenced above, the human body manufactures proteins using protein consumed, referred to as "dietary protein." The U.S. Recommended Daily Allowance for protein is 56 grams of protein per day for men aged 19-70 and 46 grams of protein per day for women aged 19-70. Men and women who are more active (including athletes) should consume higher amounts. Dietary protein can be provide from plants (referred to as "plant-derived protein") and from animals (referred to as "animal-derived protein").

Various methods of extracting proteins from a wide array plants are known. See, e.g., FR2294647A1 to Frence Luzerne; CN20081222305; WO2002/005922A1 to Petasch; U.S. Pat. No. 2,600,903 to Harry; U.S. Pat. No. 3,823,128 to Bickoff et al.; U.S. Pat. No. 3,959,246 to Bickoff et al.; U.S. Pat. No. 4,077,950 to White; U.S. Pat. No. 6,284,875 to Turpen et al.; U.S. Pat. No. 6,703,051 to Bates et al.; US Pat. Appl. Pub. No. 2008/0181999 to Yang, which are all incorporated herein by reference in their entireties.

Such methods (and others known in the art) commonly result in the provision of a protein-containing material that contains one or more components other than protein and it may be desirable to further purify the protein-containing material to decrease the content of the one or more components. As such, it would be desirable to provide further methods for extracting and/or purifying protein-containing materials, e.g., providing a purified, plant-derived protein composition for use in various products.

SUMMARY

The present disclosure provides materials derived from plants. In some embodiments, the materials are provided in what can be considered to be substantially purified form. The disclosure also provides methods for obtaining and purifying components from plants, and methods for further processing those components. In particular, the disclosure provides protein-enriched materials, as well as concentrates, isolates, and other forms of protein-containing products derived from one or more plant materials (and particularly, such concentrates, isolates, and other forms with reduced content of, e.g., chlorophyll, and/or with lighter color). The disclosure further provides methods for obtaining such protein-enriched materials, concentrates, isolates, and other forms of protein-containing products, and methods for incorporation of such protein concentrates, isolates, and other forms of protein-containing products into various types of compositions and products.

In one aspect, the disclosure provides a method for purifying a plant-derived protein-enriched material, the method comprising: a) receiving a plant-derived, protein-enriched material comprising RuBisCO, F2 fraction proteins, or a combination thereof, wherein the plant-derived, protein-enriched material further comprises undesirable color; b) treating the plant-derived, protein-enriched material with peracetic acid to give a peracetic acid-treated mixture; c) washing the peracetic acid-treated mixture with water on a filter, wherein a solid treated protein-containing material is retained on the filter; d) solubilizing the solid treated protein-containing material to give a solution and adjusting the pH of the solution to a basic pH to give a basic solution; and e) processing the basic solution on a filter to afford a retentate comprising a protein concentrate or isolate having a lighter color as compared with the plant-derived, protein-enriched material.

In certain embodiments, the undesirable color is green. The specific types of plant from which the plant-derived, protein-enriched material is obtained can vary. In certain embodiments, the plant-derived, protein-enriched material comprises material from a plant comprising green leaves. In some embodiments, the plant-derived, protein-enriched material comprises material from a plant selected from the group consisting of trees, bushes, grasses, ferns, vines, mosses, algae, herbs, or a combination thereof. In certain specific embodiments, the plant-derived, protein-enriched material comprises material from a plant selected from the group consisting of spinach, alfalfa, Swiss chard, kale, chicory, amaranth, barley leaves, mustard greens, clover, carrot leaves, beet leaves, greases (e.g., wheatgrass, orchard grass, and/or switchgrass) and combinations thereof. In certain embodiments, the plant-derived, protein-enriched material comprises material from alfalfa, and in certain embodiments, the plant-derived, protein-enriched material consists essentially of material from alfalfa.

In some embodiments, the treating step b) is conducted at a pH of about 3 to about 5. The treating step b) is, in some embodiments, conducted at a temperature of about 25° C. to about 42° C. In some embodiments, the treating step b) comprises treating the plant-derived, protein-enriched material with peracetic acid in the form of an aqueous solution comprising at least about 3% by weight peracetic acid.

In some embodiments, step c) comprises washing the peracetic acid-treated mixture with water on a 1.4 µm pore filter. In some embodiments, step c) comprises washing the peracetic acid-treated mixture with water having a pH of less than about 5.

In some embodiments, step d) comprises resolubilizing the solid treated protein-containing material in an aqueous solution. In some embodiments, step e) comprises processing the basic solution on a 10 nm filter. The disclosed method can, in some embodiments, further comprise spray drying the protein concentrate or isolate.

In certain embodiments, the protein concentrate or isolate comprises about 60% or more RuBisCO, F2 fraction proteins, or a combination thereof by weight. In additional embodiments, the protein concentrate or isolate comprises about 70% or more or about 80% or more RuBisCO, F2 fraction proteins, or a combination thereof by weight. For example, the protein concentrate or isolate can comprise about 60% or more RuBisCO by weight, about 70% or more RuBisCO by weight, or about 80% or more RuBisCO by weight. In further embodiments, the disclosed method further comprises incorporating the protein concentrate or isolate into a composition for human or animal consumption.

In another aspect, the present disclosure provides dietary supplements, foods, beverages, personal care items, pharmaceutical products, or pet foods comprising the protein composition (e.g., concentrate or isolate) described herein or made by the processes described herein.

BRIEF DESCRIPTION OF THE DRAWINGS

In order to provide an understanding of embodiments of the invention, reference is made to the appended drawings, which are not necessarily drawn to scale, and in which reference numerals refer to components of exemplary embodiments. The drawings are exemplary only, and should not be construed as limiting the invention.

FIG. 5 is a table showing recovery of protein from alfalfa and protein based on total unharvested plants in the field.

DETAILED DESCRIPTION

Figure 1:
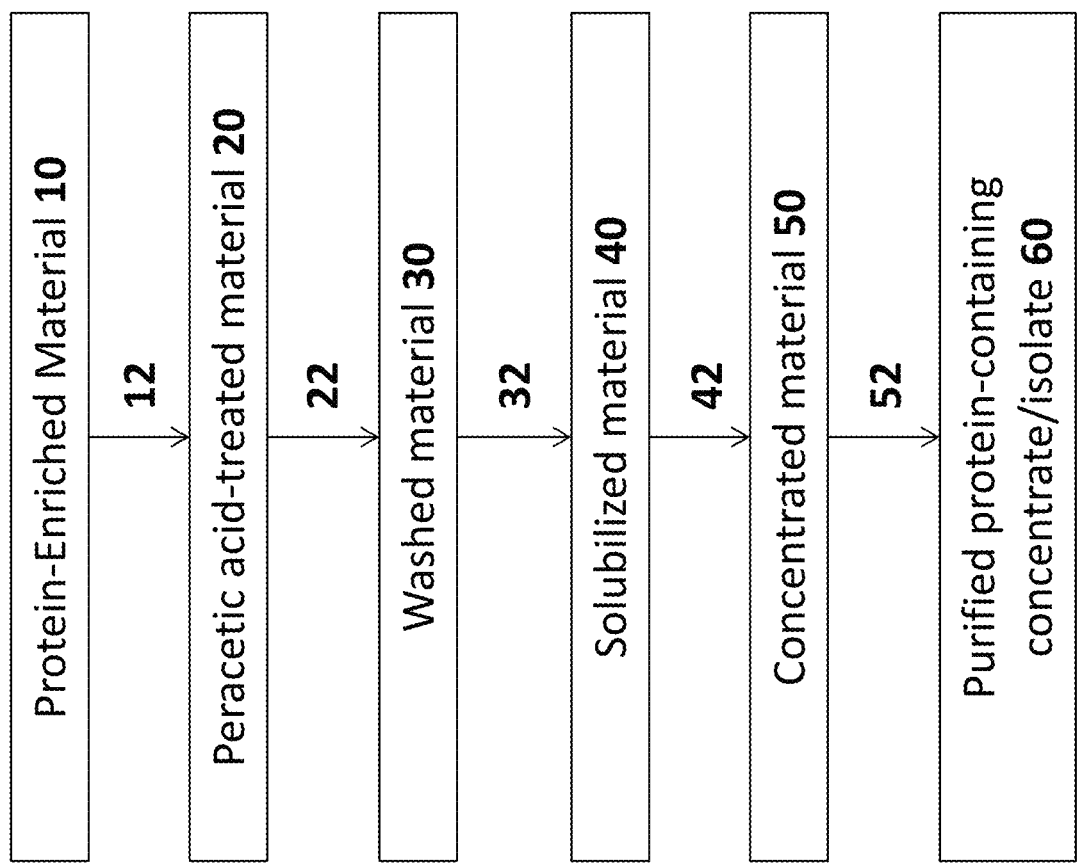
FIG. 1 is a flow chart of method steps associated with certain embodiments of the present disclosure.

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art. As used in this specification and the claims, the singular forms "a," "an," and "the" include plural referents unless the context clearly dictates otherwise. Reference to "dry weight percent" or "dry weight basis" refers to weight on the basis of dry ingredients (i.e., all ingredients except water).

Generally, the present disclosure provides methods for obtaining and/or purifying biomass-derived protein extracts. The method for obtaining biomass-derived protein extracts generally comprises extracting a biomass with a solvent and subjecting the resulting extract to various processing steps, e.g., including, but not limited to, filtration steps. Often, methods of deriving protein from various biomasses results in a protein-enriched material that is not pure protein and may contain various other components extracted from the biomass. For example, in certain embodiments, the crude protein-enriched material extracted from the biomass can further comprise such substances as lipids, chlorophyll, tannins, minerals, plant structural components, and phenolic pigments.

The methods described herein are largely suitable for obtaining and/or purifying protein-enriched material derived from any plant comprising green leaves and/or any plant believed to comprise proteins. In some embodiments, the methods are applicable to trees, bushes, grasses, ferns, vines, mosses, algae, and herbs. For example, the methods for preparing and purifying a protein-enriched material according to the present disclosure are in some embodiments applicable to such plants as spinach, alfalfa, Swiss chard, kale, chicory, amaranth, barley leaves, mustard greens, clover, carrot leaves, beet leaves, and combinations thereof, as well as various types of grasses (including, but not limited to, wheatgrass, orchard grass, and switchgrass).

A harvested portion or portions of the plant can be physically processed prior to extraction/purification. A portion or portions of the plant can be separated into individual parts or pieces (e.g., roots can be removed from stalks, stems can be removed from stalks, leaves can be removed from stalks and/or stems, petals can be removed from the remaining portion of the flower). Although any single part of the plant or multiple parts of the plant can be used according to the presently disclosed method, preferably leaves can be used, although in some embodiments, stalk or both stalk and leaves are used. The harvested portion or portions of the plant can be further subdivided into parts or pieces (e.g., shredded, cut, comminuted, pulverized, milled or ground into pieces or parts that can be characterized as filler-type pieces, granules, particulates or fine powders). The harvested portion or portions of the plant can be subjected to external forces or pressure (e.g., by being pressed or subjected to roll treatment). When carrying out such processing conditions, the harvested portion or portions of the plant can have a moisture content that approximates its natural moisture content (e.g., its moisture content immediately upon harvest), a moisture content achieved by adding moisture to the harvested portion or portions of the plant, or a moisture content that results from the drying of the harvested portion or portions of the plant.

As noted herein above, according to the present disclosure, protein-enriched material is provided via treatment of a harvested plant material (also referred to herein as "biomass" or "plant biomass"). The biomass may be any one of a variety of plant types or a combination of two or more plant types. The term "biomass" and related terms such as "biomatter," "plant biomass," and "plant source" are understood to refer to any portion of a harvested plant that may be processed to extract, separate, or isolate components of interest therefrom. The processing may be carried out in relation to various plants or portions thereof, such as seeds, flowers, stalks, stems, roots, tubers, leaves, and/or any further portions of the plant. The plant can be harvested in either an immature or mature form, and is typically processed (e.g., extracted) in green form.

The plant biomass can be subjected to various treatment processes prior to extraction and/or purification such as, refrigeration, freezing, drying (e.g., freeze-drying or spray-drying), irradiation, yellowing, heating, cooking (e.g., roasting, frying or boiling), fermentation, bleaching or otherwise subjected to storage or treatment for later use. In some embodiments, harvested plant material can be sprayed with a buffer or antioxidant (e.g., a sodium metabisulfite buffer) to prevent the green plants from browning prior to further treatment as described herein. Other exemplary processing techniques are described, for example, in US Pat. Appl. Pub. Nos. 2009/0025739 to Brinkley et al. and 2011/0174323 to Coleman, III et al., which are incorporated by reference herein. At least a portion of the plant can be treated with enzymes and/or probiotics before or after harvest, as discussed (with respect to plants of the *Nicotiana* species) in U.S. patent application Ser. No. 13/444,272 to Marshall et al., filed on Apr. 11, 2012 and U.S. patent application Ser. No. 13/553,222 to Moldoveanu, filed on Jul. 19, 2012, which are incorporated herein by reference.

The disclosure, in some embodiments, provides methods for obtaining protein-enriched materials, generally comprising receiving a plant material; contacting the plant material with a solvent for a time and under conditions sufficient to extract one or more proteins from the plant material into the solvent and form a liquid protein-containing extract; separating a solid extracted plant material from the liquid protein-containing extract; clarifying the liquid protein-containing extract to form a clarified protein-containing extract and a solids fraction; and treating the clarified protein-containing extract so as to provide a protein-enriched material comprising a relatively high percentage of protein by dry weight (e.g., at least about 60% protein by dry weight).

By "protein-enriched material" is meant a material (e.g., an extract) that has been derived from a plant and which contains one or more types of protein. The crude protein-enriched materials described herein generally comprise an amount of undesirable components/impurities such as ash, metal salts, trace metals, precipitates, chlorophyll, and other residual materials. Further, the protein-enriched materials may exhibit undesirable sensory or organoleptic characteristics (e.g., taste characteristics, odor, and/or color).

The disclosure also provides a method of further processing such a protein-enriched material (obtained from the method referenced herein above or by other methods), to provide a purer protein composition, such as a composition in the form of a concentrate or isolate. By "protein concentrate" as used herein is meant a material comprising between about 29% and about 89% by weight protein on a dry weight basis. By "protein isolate" as used herein is meant a material comprising about 90% or more protein by weight on a dry weight basis. In some embodiments, the disclosure provides methods for purifying protein-enriched materials to provide concentrates and/or isolates containing minimal amounts of certain undesirable components/impurities. With respect to various types of plant materials as described herein, the process can, in some embodiments, isolate protein from all the other plant compounds, including, but not limited to, starches, fiber, sugars, ash and other molecules, chlorophyll etc.

Various methods disclosed herein can provide purified plant-derived protein concentrates and isolates with little to no coloration (e.g., little to no green coloration). Advantageously, the disclosed purification methods effectively remove chlorophyll/color from the material. The ability to remove color is unique, as many other plant-derived proteins are not extracted from green leaf; where (as in most embodiments outlined herein), the protein is derived from green leaf, coloration is often considered undesirable in the context of a protein concentrate/isolate, and is advantageously removed (as provided herein). In some embodiments, the disclosed purification methods further remove undesirable taste/flavor (e.g., a perceived "vegetable-like" flavor).

In some embodiments, the processes can be tailored for obtaining and/or purifying protein-enriched materials comprising one or more specific protein types or may be used for mixtures of two or more proteins with different properties, e.g., different solubilities, compound types, compound chemical properties, compound physical properties, or the like. Generally, the water-soluble portion of plant biomass consists of two fractions. One fraction predominantly comprises RuBisCO, whose subunit molecular weight is about 550 kD. RuBisCO may comprise up to about 25% of the total protein content of a leaf and up to about 10% of the solid matter of a leaf. A second fraction ("Fraction 2 protein" or "F2 protein") generally contains a mixture of proteins and peptides with molecular weights ranging from about 3 kD to about 100 kD and may also contain other compounds including sugars, vitamins, alkaloids, flavors, and amino acids.

In particular embodiments, the protein(s) of the protein-enriched material obtained and/or treated according to the methods provided herein (as well as the protein(s) in the resulting concentrate and/or isolate described) comprise RuBisCO and/or F2 proteins. In particular, RuBisCO is ribulose-1,5-bisphosphate carboxylase oxygenase and is largely considered to be the most abundant protein in the world, as it is present in every plant that undergoes photosynthesis. RuBisCO is essential to the initial step of the photosynthetic fixation of carbon dioxide and functions to catalyze the carboxylation and/or oxygenation of ribulose-1,5-bisphosphate. For many applications (e.g., food products, feed products, and industrial products), it may be desirable to replace certain animal proteins with plant proteins. Additionally, in some applications, it may be desirable to replace certain other plant proteins (e.g., soy proteins and/or genetically modified proteins). RuBisCO has been found to exhibit good nutritional properties and is colorless, tasteless, and odorless. Further, certain physical properties of RuBisCO render it advantageous for use in such products, as it has excellent binding, gelling, solubility, and emulsifying behavior.

Various methods have been proposed for the extraction of RuBisCO and/or other proteins from a wide array of plant materials. For example, see U.S. Pat. No. 4,268,632 to Wildman et al., U.S. Pat. No. 4,340,676 to Bourke; U.S. Pat. No. 4,400,471 to Johal; U.S. Pat. No. 4,588,691 to Johal; and U.S. Pat. No. 6,033,895 to Garger et al., which are incorporated herein by reference in their entireties. Exemplary means for extracting RuBisCO from alfalfa, for example, are described in Pick-Seng et al., J. Food Sci., 1972, Vol. 37(1): pp. 94-99, Kobbi et al., Waste and Biomass Valorization, March 2017, Vol. 8(2); pp. 493-504, and Lamsal et al., LWT, 2007, Vol. 40; pp. 1520-1526, which are incorporated herein by reference in their entireties. In certain embodiments, protein-enriched materials are prepared according to methods comparable to those described in U.S. Pat. No. 9,301,544 to Mua et al., which is incorporated herein by reference, the subject matter of which is outlined briefly herein.

According to the disclosure of the '544 patent, one exemplary set of processing steps that can be carried out to obtain a RuBisCO-enriched extract and/or a F2 protein-enriched extract from a plant or portion thereof can include the following steps. A plant material is homogenized to provide a solid pulp and a liquid, protein-containing extract ("green juice"). The extract is clarified to remove solids therefrom, giving a solids fraction and a clarified, protein-containing extract. The extract is then pH-adjusted and separated into a liquid component and a solid, protein-containing precipitate. The precipitate generally comprises RuBisCO as well as various additional components. The pH at this step is advantageously maintained between 6.5 and 8, which in some embodiments is maintained throughout the purification process. Where a significant amount of F2 fraction is contained in the liquid component, that liquid component can be treated, for example, by filtration (e.g., through a filter or membrane on which the F2 proteins are generally retained, while allowing certain remaining components to pass through).

An alternative exemplary process disclosed in the '544 patent for the production of a RuBisCO- and F2 protein-enriched material, RuBisCO-enriched material, and/or F2 protein-enriched material comprises the following steps. A plant material can be homogenized to provide a solid pulp and a liquid, protein-containing extract. The extract can then be clarified to remove solids therefrom (e.g., via a pH-adjustment step to provide an acidic or basic clarified, protein-containing extract), giving a solids fraction and a clarified, protein-containing extract. The extract is filtered and washed to give a solid, RuBisCO-enriched material, and a permeate. In certain embodiments, the permeate may comprise F2 proteins and the permeate can optionally be processed (e.g., including via filtration methods) to give an F2 protein-enriched material.

Any modifications to the steps of these methods to provide a protein-enriched material which are functionally equivalent to the procedures and conditions generally disclosed herein or in the '544 patent are within the scope of the instant disclosure. For example, typical separation processes can include one or more process steps such as solvent extraction (e.g., using polar solvents, organic solvents, or supercritical fluids), chromatography (e.g., preparative liquid chromatography), clarification, distillation, filtration (e.g., ultrafiltration), recrystallization, and/or solvent-solvent partitioning. In some embodiments, it may be advantageous to conduct solvent extraction using a cold extracting liquid (e.g., water), particularly prior to a subsequent filtration step. Extractions are commonly conducted at elevated temperature; however, subjecting extracts resulting from such extractions directly to filtration may damage the filters, due to the heat associated with the extracts and, as such, hot/warm extracts are typically cooled prior to subsequent filtration steps. This cooling step can be avoided in some embodiments by conducting extractions at room temperature, in which case the resulting extracts can be advantageously directly treated by filtration. In some embodiments, the plant or portion thereof can be pre-treated, e.g., to liberate certain compounds to make the desired compounds available for more efficient separation. In some embodiments, multiple methods are used to obtain the desired compounds.

Although protein-enriched material 10 may advantageously be obtained according to a method comparable to that outlined in U.S. Pat. No. 9,301,544, as referenced herein above, the disclosure is not understood to be limited to protein-enriched material 10 obtained in this manner. Other exemplary techniques for extracting protein from plant materials that can be used for the provision of protein-enriched material 10 are not particularly limited. Other exemplary means for extraction of proteins from plant materials include, but are not limited to, those described in U.S. Pat. No. 7,337,782 to Thompson; U.S. Pat. No. 6,033,895 to Garger et al.; U.S. Pat. No. 4,941,484 to Clapp et al.; U.S. Pat. Nos. 4,588,691 and 4,400,471 to Johal; U.S. Pat. No. 4,347,324 to Kwanyuen et al., U.S. Pat. No. 4,340,676 to Bourque; U.S. Pat. No. 4,333,871 to DeJong; U.S. Pat. Nos. 4,289,147 and 4,268,632 to Wildman et al.; U.S. Pat. Nos. 3,959,246, 3,823,128, and 3,684,520 to Bickoff et al.; US Pat. Appl. Publ. Nos. 2010/0093054 to Lo et al. and 2013/0072661 to Kale; US Pat. Appl. No. Int'l Appl. Publ. Nos. WO2011/078671 to Van de Velde et al. and WO2008/143914 to Lo; and EP Pat. Publ. Nos. EP 2403888 to Parker et al.; EP 1691759 to Boddupalli et al.; and EP 1067946 to Brinkhaus et al., which are all incorporated by reference herein in their entireties. Other exemplary processing methods are provided, for example, in U.S. Pat. No. 9,220,295 to Morton et al., which is incorporated herein by reference.

The protein-enriched material 10 used as a starting point in the purification processes discussed herein can be provided in varying forms. In some embodiments, the protein-enriched material is provided in a moistened form. In some embodiments, the protein-enriched extract is subjected to a solvent removal process such that the extract achieves a predominantly solid form. The protein-enriched extracts may be provided in a low solvent form. By the term "low solvent form" is meant that the solvent content including the moisture content of the material (e.g., a protein-enriched extract) is less than about 12 percent, based on the total weight of the material. Convenient methods for providing the protein-enriched extract in low solvent form include spray drying, freeze drying, belt drying, flash drying, or other such methods. It is particularly desirable to concentrate the liquid extract prior to spray drying or freeze drying the extract. A representative spray drying process is described in U.S. Pat. No. 3,398,754 to Tughan, which is incorporated herein by reference. A representative freeze drying process is described in U.S. Pat. No. 3,316,919 to Green, which is incorporated herein by reference. Methods and conditions for providing extracted materials in a low solvent or solid form (e.g., as a powder) will be apparent to the skilled artisan.

The protein-enriched material 10 typically comprises some percentage of undesirable components and/or features. According to the present disclosure, a protein-containing material (which may, in some embodiments, comprise RuBisCO and/or F2 proteins) isolated from a plant material (e.g., according to various methods as outlined above) is further treated to provide a protein composition (e.g., in the form of a concentrate or isolate) having a lower concentration of one or more of these undesirable components than prior to treatment.

Generally, the methods disclosed herein involve treatment of a protein-enriched material with peracetic acid and/or with hydrogen peroxide, as will be described in further detail herein. In certain embodiments, the treatment process is that illustrated in FIG. 1. Generally, the treatment process of FIG. 1 involves a solid material comprising protein (10), typically prepared by extracting a plant material to give an aqueous extract and concentrating the extract (as described in detail herein above). Material 10 is subjected to the following steps: 12 (treating material 10 with peracetic acid, giving peracetic acid-treated material 20), 22 (washing peracetic acid-treated material 20 with water on a relatively large, e.g., micron-sized (e.g., 1.4 µm) filter to give washed material 30), 32 (solubilizing washed material 30 and pH adjusting to a basic pH, e.g., about 10 or greater, to give solubilized material 40), 42 (concentrating the solubilized material to give concentrated material 50), and 52 (washing concentrated material 50 on a relatively small, e.g., nanometer-sized (e.g., 10 nm) filter to give purified protein-containing concentrate/isolate 60).

Step 12 involves treating the protein-containing material 10 with peracetic acid to give peracetic acid-treated material 20. Optionally, prior to the addition of peracetic acid, material 10 is first pretreated to a pH of about 3-6, e.g., around 5, which can be achieved using various acids, e.g., including, but not limited to, acetic acid.

Commercially available peracetic acid is generally provided as an aqueous solution and typically contains some concentration of peroxide ($H_2O_2$). Thus, step 12 typically comprises treating material 10 with peracetic acid and peroxide in aqueous solution. The amount of peracetic acid employed in this step can vary, but in some embodiments is an amount of about 0.75% to about 5% peracetic acid by weight or about 1% to about 3% peracetic acid by weight, e.g., about 1% peracetic acid by weight (and about 1% to about 10% peroxide or about 3% to about 8% peroxide, e.g., about 3.5% peroxide by weight), based on the mixture of material 10, peracetic acid, peroxide, and water provided by the peracetic acid/peroxide solution. The contacting can be done at varying temperatures, but in some embodiments, it may enhance the treatment to employ heating during at least a portion of step 12. For example, in certain embodiments, the mixing of protein-enriched material 10, peracetic acid and peroxide can be done at a temperature greater than room temperature, e.g., about 30° C. or greater, or about 35° C. or greater, such as about 25° C. to about 42° C. or about 30° C. to about 42° C., such as about 40° C.±2° C. The heating temperature is generally maintained at or below about 42° C. to avoid denaturing the protein. The amount of time for which the protein-containing material 10 is maintained in contact with the peracetic acid/peroxide solution can vary, but is generally at least about 1 hour, at least about 2 hours, or at least about 3 hours (e.g., about 1 to about 5 hours or about 2 to about 5 hours, such as about 3 hours). The pH of the mixture is typically acidic; in some embodiments, the pH is maintained below about 4, e.g., about 3.5 or lower.

The resulting peracetic acid-treated material 20 is typically in the form of a suspension, as the protein present therein is typically precipitated at low pH. Peracetic acid-treated material 20 is next subjected to a washing step 22. Material 20 is typically placed on a relatively large pore size filter sufficient to retain the protein (RuBisCO and/or F2 protein) on the surface of the filter. For example, material 20 can be put on a micron-sized pore filter, such as a 1.4 μm filter (e.g., a 1.4 μm ceramic filter). In some embodiments, tangential flow filtration is used. The washing step 22 involves contacting material 20 with purified water on the filter, allowing the water to remove undesirable components, and retaining the protein on the surface of the filter. The water employed in the washing step advantageously has a pH of less than 7 (i.e., somewhat acidic) to ensure that the protein does not solubilize/stays in a precipitated state, and does not pass through the filter (resulting in loss of desired material). For example, the water advantageously has a pH of about 5 or less or about 4 or less (e.g., purified water with a pH of about 3.5) and can, in some embodiments, be USP water. The water used in washing step 22 is understood, e.g., to quench the peracetic acid remaining from acid treatment step 12 and remove residual peracetic acid (along with possibly other components) from the peracetic acid-treated material 20, which remains on the surface of the filter. The amount of water used to wash material 20 can vary; however, a significant amount of water is generally employed to ensure removal of at least a majority of the peracetic acid from the sample. Similarly, the number of washings conducted can vary, but, again, a sufficient number of washings to ensure removal of at least a majority of the peracetic acid from the sample is preferred. Although not limited thereto, the washing is advantageously conducted based on 2 to 10 times the volume of retentate and, as such, the amount of water employed in the washing (amount per washing and number of washings) may depend upon the volume of material being washed. Washing step 22 is typically conducted at room temperature, although this step is not limited thereto.

The resulting retentate/washed material 30 is then re-solubilized in step 32. The liquid(s) used to solubilize material 30 is advantageously basic (as the proteins are understood to precipitate at low pH and solubility is enhanced as pH is increased). Consequently, step 32 typically involves contacting material 30 with water and base. The specific base can vary, so long as it is capable of providing the desired pH and solubilizing the protein-containing material 30. In some embodiments, a solution of sodium hydroxide (NaOH) is used to achieve the desired pH. The pH of the solution in which material 30 is solubilized during this step is typically about 8 or greater or about 10 or greater, e.g., about 8 to about 16 or about 8 to about 12 (e.g., about 10.5). In some embodiments, the liquid used to solubilize material 30 further comprises a buffer. For example, in one embodiment, a buffer comprising sodium bicarbonate and potassium carbonate is used (which may include various other components that do not negatively interfere with the resolubilization of the protein, e.g., including, but not limited to, sodium metabisulfite). Inclusion of a buffer can, in some embodiments, aid in ensuring the material 30 goes into solution; however, it adds salt content and thus may require a greater extent of washing at a later step to ensure removal of the salts.

The resulting solubilized protein-containing material, in the form of solubilized material 40, is then concentrated (step 42) to give a concentrated material 50. Concentration can be done using methods known in the art for the removal of at least a majority of the liquid associated with solution 40. In preferred embodiments, tangential flow filtration can be used to concentrate the material. Using tangential flow filtration, the material 40 is put on a nanometer-sized pore filter, such as a 10 nm filter (e.g., a 10 nm ceramic filter). Advantageously, the pore size of the filter in step 42 is relatively low; however, the pore size should not be significantly lower than 10 nm, as such pore sizes will likely lead to retention of salts and other undesired components on the surface of the filter. The retentate from this process then comprises concentrated material 50. In some embodiments, concentration can be done by evaporation at room temperature and atmospheric pressure and/or can employ elevated heat (up to about 45° C. or up to about 42° C. to avoid denaturing the protein) and/or applying vacuum). Typically, the material is concentrated so that the material is in substantially solid form, although some liquid may still be associated with concentrated material 50.

The resulting material 50 is then washed 52 in a similar manner as in step 22. However, step 52 generally is conducted on a relatively small pore size filter. For example, material 40 can be put on a nanometer-sized pore filter, such as a 10 nm filter (e.g., a 10 nm ceramic filter). Advantageously, the pore size of the filter in step 52 is relatively low; however, the pore size should not be significantly lower than 10 nm, as such pore sizes will likely lead to retention of salts and other undesired components on the surface of the filter. In some embodiments, tangential flow filtration is used. The washing step 52 involves contacting material 50 with purified water on the filter, allowing the water to remove undesirable components, and retaining the protein on the surface of the filter. The water employed in this washing step may, in some embodiments, be purified water (e.g., having a neutral pH of ~7) or may be USP water, which has a lower pH. The protein is already in precipitated form at this stage of the process and the small pore size of the filter on which the material is washed typically prevents significant passage of desired protein through the filter.

The water used in washing step 52 is understood, e.g., to remove residual base and salts (along with possibly other components) from the protein-containing material 50, which remains on the surface of the filter. The amount of water used to wash the protein-containing material can vary; however, a significant amount of water is generally employed to ensure removal of at least a majority of the base and salts from the sample. Similarly, the number of washings conducted can vary, but again a sufficient number of washings to ensure removal of at least a majority of the base and salts from the sample is preferred. Although not limited thereto, the washing is advantageously conducted based on 2 to 10 times the volume of retentate and, as such, the amount of water employed in the washing (amount per washing and number of washings) may depend upon the volume of material being washed. Washing step 52 is typically conducted at room temperature, although this step is not limited thereto. In certain embodiments, steps 42 and 52 are combined, such that concentration and washing are conducted substantially together. For example, in certain embodiments, tangential flow filtration is employed, which can serve multiple functions, e.g., washing and concentrating the protein-containing material.

Advantageously, material 60 (purified protein-containing concentrate/isolate) is provided in dried or substantially dried form following the washing treatment. The drying can be conducted by concentration/evaporation and/or spray drying by methods known in the art. In one preferred embodiment, the material is spray dried, e.g., at elevated temperatures. One exemplary set of conditions for the spray drying is 180° C. inlet/80° C. outlet.

Purified protein-containing material 60 generally is lighter in color than material 10 and is lighter in color than a comparable material that has not been subjected to a process comprising steps 12, 22, 32, 42, and 52 as outlined herein above. In some embodiments, the treated material 60 exhibits a lighter color (e.g., a light cream/tan color which is lighter in color and/or contains less green coloration than the material 10 subjected to treatment). In some embodiments, treated material (purified protein-containing concentrate/isolate 60) has decreased ash and/or decreased fiber with respect to the protein-containing material prior to treatment (i.e., protein-enriched material 10). In some embodiments, purified protein-containing material 60 exhibits less undesirable flavor characteristics than material 10 and can, in some embodiments, be considered largely "tasteless." For example, in some embodiments, protein-containing material 10 is at least about 40% protein, e.g., about 40% to about 60% pure protein by dry weight and the corresponding purified protein-containing concentrate/isolate 60 is at least about 50%, at least about 60%, or at least about 65% pure protein by dry weight. As such, the peracetic acid treatment process as described herein above can, in some embodiments, lead to an increase in purity of a protein-containing material of about 10% or more or about 20% or more.

Other methods of purification can, in some embodiments, be used prior to or after the peracetic acid treatment disclosed herein. For example, in some embodiments, the material can be treated to further remove, e.g., taste or odor as generally outlined in U.S. Pat. No. 9,175,052, which is incorporated herein by reference in its entirety. In certain embodiments, a tasteless, colorless, and/or odorless protein concentrate or isolate is provided according to the methods described herein.

Advantageously, in certain embodiments, the protein composition provided via the disclosed purification method can thus exhibit less green color as compared with the protein-enriched extract. As such, the disclosed peracetic acid treatment method can significantly decrease the color of the material subjected to the method. For example, in certain embodiments, the methods outlined herein can provide a material that is visually lighter in color. In certain embodiments, a material exhibiting no green coloration is obtained. Such changes in color resulting from the disclosed method can be evaluated, e.g., via visual inspection or by analytical optical methods such as light absorption/spectroscopy (e.g., determining how much of the green wavelengths are absorbed by the material).

The protein composition can, in some embodiments, comprise a higher content of protein than the protein-enriched extract prior to peracetic acid treatment. For example, in some embodiments, the supercritical extraction described herein can provide at least about a 5%, 10%, 15%, 20%, or 25% increase in protein content by weight. Accordingly, the protein composition following supercritical extraction generally comprises at least about 50%, at least about 60%, at least about 70%, at least about 80%, at least about 90%, at least about 95%, at least about 98%, or at least about 99% protein (e.g., RuBisCO and/or F2 proteins) by dry weight.

The form of the protein composition provided according to the present disclosure (e.g., a RuBisCO concentrate or isolate, combined RuBisCO/F2 protein concentrate or isolate, and/or F2 concentrate or isolate) obtained according to the methods of the present disclosure can vary. Typically, these materials are in solid, liquid, or semi-solid or gel forms. The resulting formulations can be used in concrete, absolute, or neat form. Solid forms of the concentrates or isolates described herein can include spray-dried and freeze-dried forms. Liquid forms of the concentrates or isolates described herein can include formulations contained within aqueous or organic solvent carriers.

The methods disclosed herein may, in some embodiments, provide a protein concentrate or isolate comprising at least about 50%, at least about 60%, at least about 70%, at least about 80%, or at least about 90% protein by dry weight. In some embodiments, the protein concentrate or isolate comprises a mixture of RuBisCO and F2 proteins. In some embodiments, the protein in the protein concentrate or isolate comprises primarily RuBisCO. In some embodiments, the protein concentrate or isolate comprises at least about 50%, at least about 60%, at least about 70%, at least about 80%, or at least about 90% RuBisCO protein by weight. In some embodiments, the present disclosure specifically provides a method for the isolation and/or purification of RuBisCO extracted from a plant of the *Nicotiana* species or a portion thereof. Accordingly, the methods disclosed herein may, in some embodiments, provide a RuBisCO concentrate or isolate, e.g., a material comprising at least about 50%, at least about 60%, at least about 70%, at least about 80%, or at least about 90% RuBisCO by dry weight.

Although in some embodiments, the protein concentrate or isolate described herein can be used directly following the one or more treatment steps, it may be desirable to thermally treat the material in order to, for example, pasteurize the material or otherwise chemically alter the material. See, for example, US Pat. Pub. No. 2010/0300463 to Chen et al., which is incorporated herein by reference. In some embodiments, in addition to or in place of the optional heat treatment, plant material can be irradiated (e.g., to ensure no microbes are associated with the protein concentrate or isolate).

The protein concentrates and isolates (i.e., RuBisCO concentrates and isolates, combined RuBisCO/F2 protein concentrates and isolates, and/or F2 protein concentrates and isolates) provided following any one or more of the purification treatment processes described herein can advantageously be used in various applications. For many applications (e.g., food products, feed products, and industrial products), it may be desirable to replace certain animal proteins with plant proteins. Additionally, in some applications, it may be desirable to replace certain other plant proteins typically used (e.g., soy proteins and/or genetically modified proteins). Protein concentrates and isolates such as those provided by the methods described herein can exhibit good nutritional properties and, in some embodiments, can be provided in a form that has a reduced content of various undesirable components, and/or good sensory characteristics (e.g., color), making them particularly suitable for use in various products. Further, certain physical properties of RuBisCO render it advantageous for use in such products, as it has excellent binding, gelling, solubility, and emulsifying behavior. In some embodiments, the types of treatment described herein may provide a food-grade protein-containing material. In certain embodiments, the protein concentrate isolate comprises a protein material that exceeds soy protein in nutritional quality. In some embodiments, the protein concentrate or isolate may be useful for medicinal purposes.

Processed materials that are provided in accordance with the present disclosure are useful ingredients for a wide variety of commercial applications. The materials can be used as binders, fillers or extenders, or can serve other functions or impart functional attributes, in a wide variety of industrial formulations. For example, the materials can be used as components of various types of resins that have industrial applications; and additionally can be used as components of coatings (e.g., for inks and paints) and of adhesives (e.g., for glues and hot melt formulations). The materials can be used as components of a wide variety of cosmetic formulations (e.g., the materials can be incorporated within shampoos and skin care products). The materials can be used as components of foods, dietary supplements and functional foods (e.g., as components of beverages, processed food products, and the like). See, e.g., U.S. Pat. No. 9,301,544 to Mua et al., which is incorporated herein by reference in its entirety. The materials also can be used components of animal feed. The materials can be used as components of pharmaceutical formulations (e.g., as components of liquids, gums, lozenges, tablets and pills that are used for medicinal purposes).

The amount of protein concentrate or isolate incorporated within compositions for such purposes can depend, for example, on the desired function of the concentrate or isolate, the chemical makeup of the concentrate or isolate, and the type of composition/product to which the concentrate or isolate is added.

EXPERIMENTAL

Aspects of the present invention are more fully illustrated by the following examples, which are set forth to illustrate certain aspects of the present invention and are not to be construed as limiting thereof.

Alfalfa is harvested and subjected to extraction via a method targeting RuBisCO, similar to that done previously for tobacco. See U.S. Pat. No. 9,301,544 to Mua et al., which is incorporated herein by reference in its entirety, which is incorporated herein by reference. Specifically, harvested alfalfa is extracted through a double stack disintegrator and screw press system. Extraction is performed with a 2:1 ratio of extraction buffer with 90% at the top of the grinder and 10% at the press. Various buffer to tissue ratios were tested due to the relatively low moisture content of the alfalfa (compared to tobacco). The ratio began at 1:1 and was increased to 2:1 incrementally during processing. Additional water was used to help spray down the plants and prevent clogging. The long pieces of alfalfa were difficult to feed and it may be useful to do additional chopping in the field (prior to extraction).

After extraction, the green juice is chilled to ≤10° C. The chilled green juice is processed through a decanter centrifuge at 4300 RPM and 30 psi of back pressure. The decanter supernatant is then further processed through the disc stack at 7200 RPM and 75 psi of back pressure. The disc stack pellet is discarded. The supernatant was then pH adjusted to 6.5 with HCl solution. The pH-adjusted supernatant is combined with 10 g/L of celupure C300 DE and is filter pressed with 1.0 μm filter pads. The press is washed with 10× volumes of extraction buffer to DE followed by a blow down with compressed air. It was noted that substantial green coloration was still in the filtrate; whereas, substantially all chlorophyll is removed by this step in the tobacco process (as evidenced by little to no green coloration during tobacco processing).

The filtrate and wash is then concentrated on a 0.1 μm ceramic system to 500 L followed by a wash of 7× volumes with wash buffer. The washed retentate is then concentrated to the system hold up volume. Half this volume is then spray dried at 180° C. inlet and 80° C. outlet. There were several recovery issues with the spray drying process caused by clogging of the cyclonic separator. This is likely due to a larger quantity of protein with lower purity relative to tobacco material. The F1 powder was "clumpy" and did not form an even dispersion with the air in the separator. The F1 was also noted very green in color. The ceramic permeate is concentrated on a 10 kDa spiral wound ultrafilter to a volume of 85 L, followed by a wash with 7× volumes of wash buffer. The 10 kDa permeate and retentate were sampled then discarded. The 10 kDa retentate could be spray dried to F2 protein at a later date.

Figure 2:
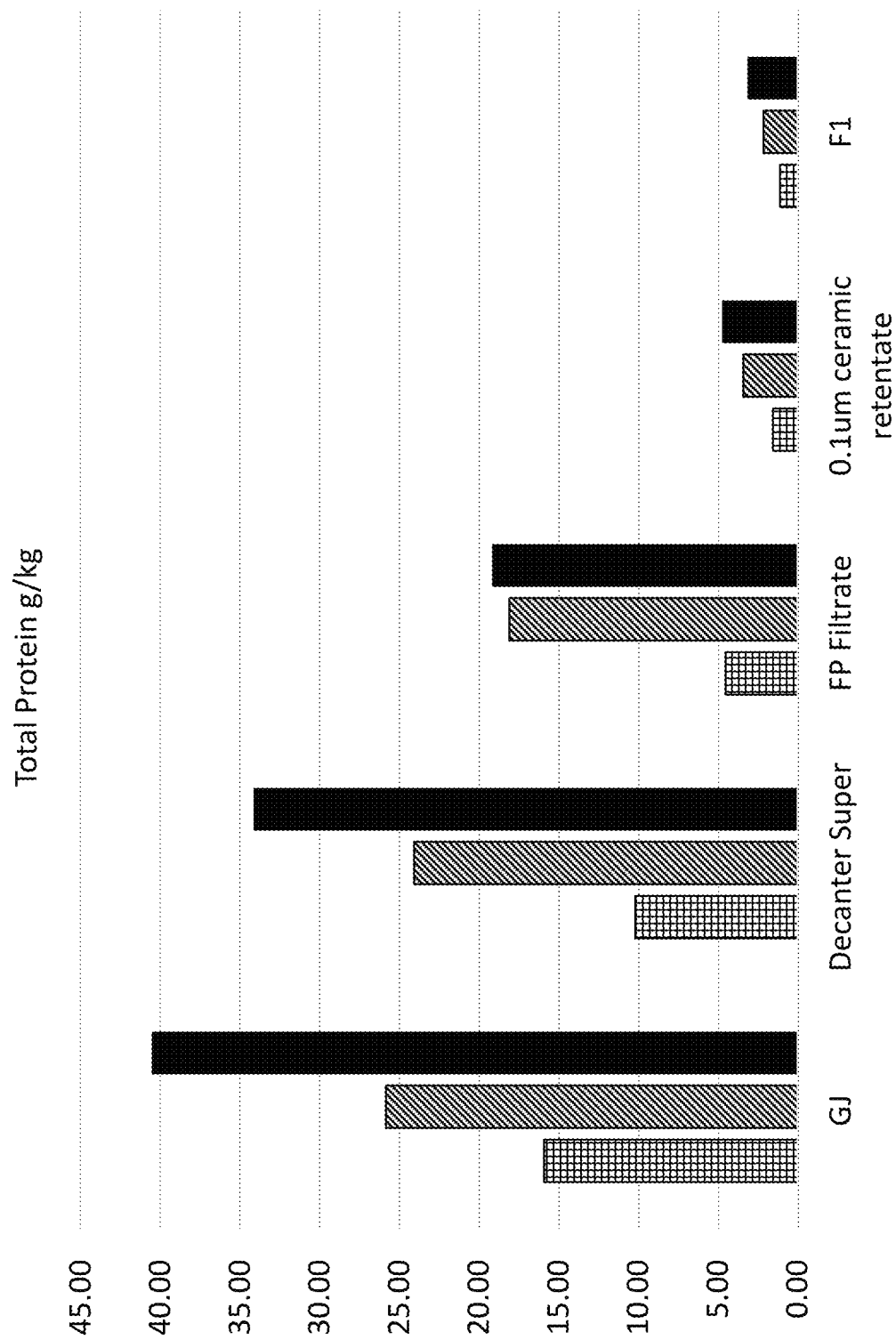
FIG. 2 is a graph of experimental findings with respect to the amount of protein obtained from alfalfa plants as compared with the amount of protein obtained from tobacco plants.
Figure 3:
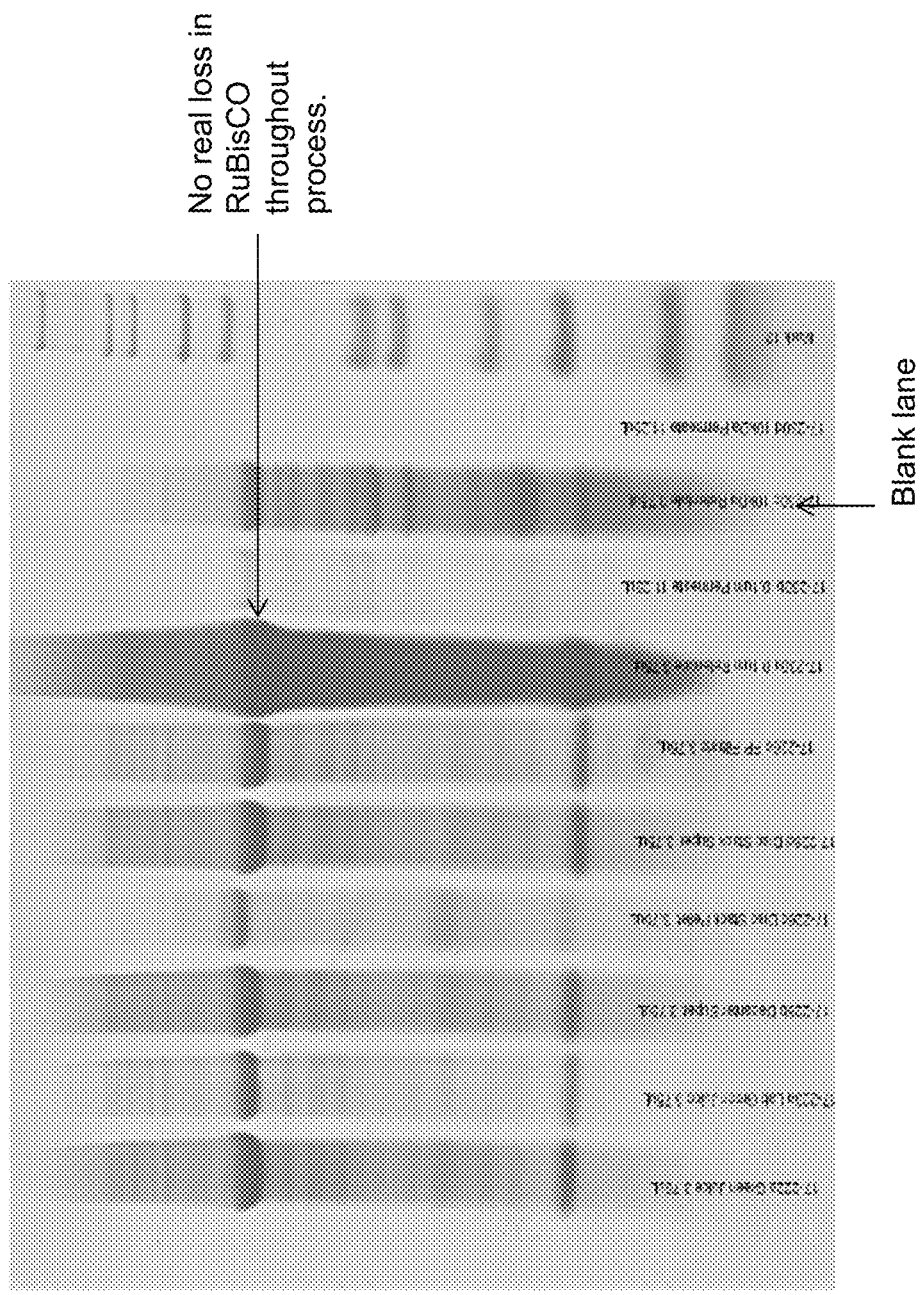
FIG. 3 demonstrates the RuBisCO present in an experimental extraction from alfalfa, showing protein present at various steps of the process.
Figure 4A:
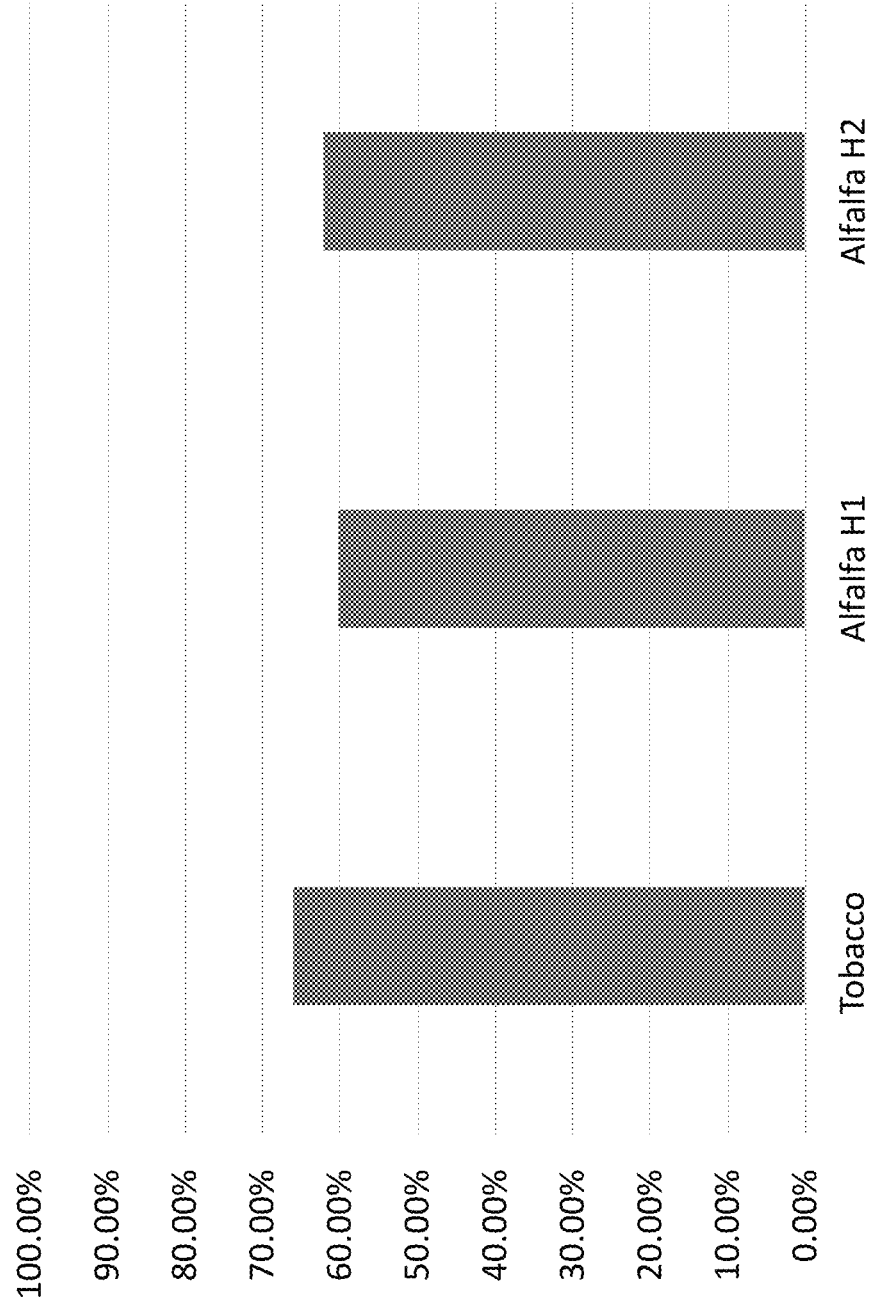
FIG. 4A is a bar graph of the purity of the RuBisCO obtained from two alfalfa extractions as compared with that of RuBisCO obtained from an experimental tobacco extraction (AAA: amino acid analysis)
Figure 4B:
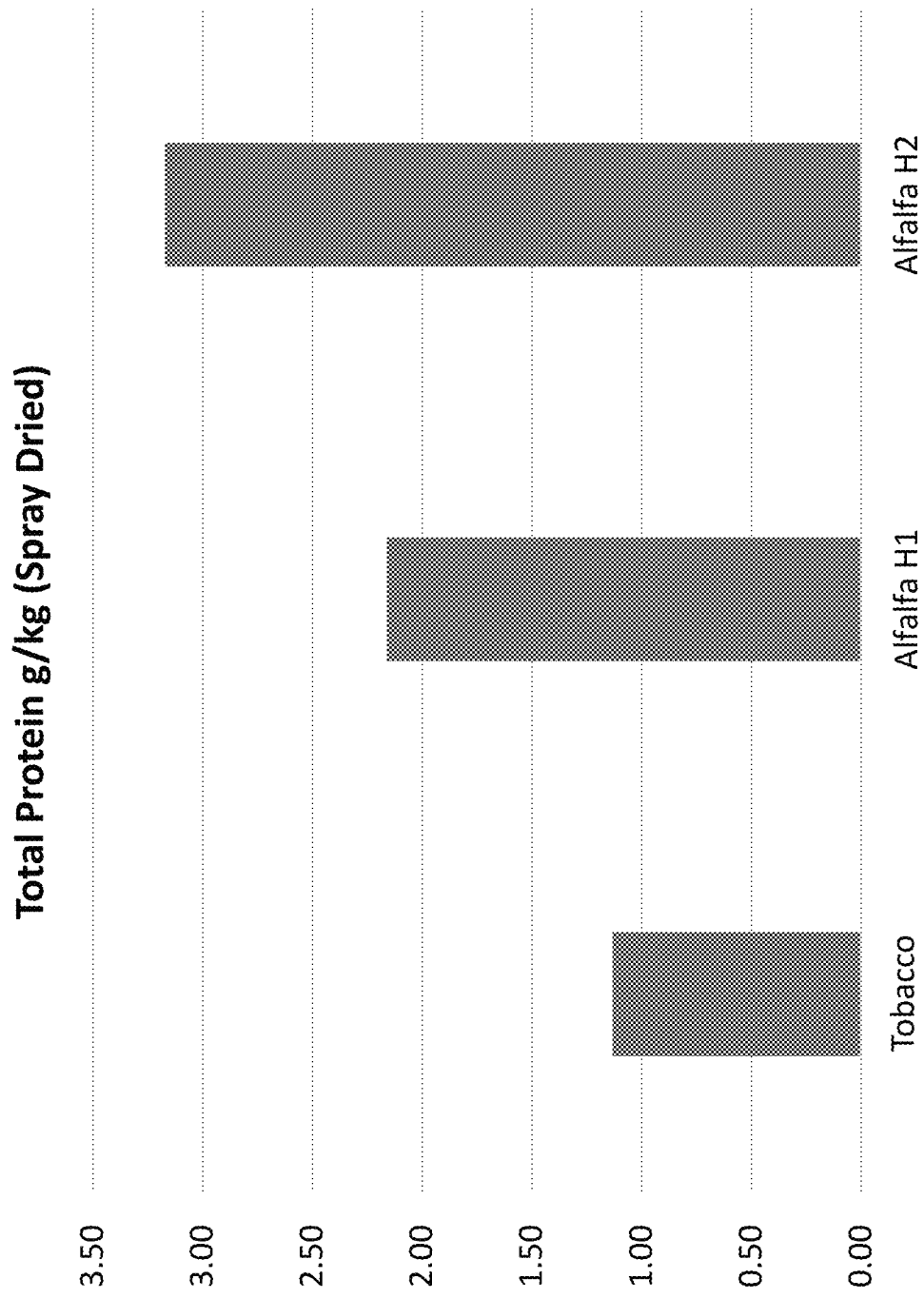
FIG. 4B is a bar graph of the total protein obtained from the alfalfa extractions and tobacco extraction shown in FIG. 4A.

Recovery of spray-dried alfalfa-obtained RuBisCO was between 2 and 3 times higher than that for the average tobacco harvests reported previously. The total protein recovery is shown in FIG. 2. Based on the blank lane (shown in FIG. 3, registering 12.7 g/kg of protein), it is determined that alfalfa must contain large quantities of small peptides (the 10 kDa retentate indicates a large amount of non-RuBisCO proteins). It is noted that alfalfa appeared to have a high content of other proteins besides RuBisCO that were not captured via this process. The protein purity and content as compared with tobacco-derived protein is shown in FIGS. 4A and 4B. FIG. 5 provides a comparison between the total number of RuBisCO obtained per acre of alfalfa planted versus the total amount of RuBisCO obtained per acre of tobacco planted.

The resulting spray-dried alfalfa-obtained RuBisCO exhibited a distinct green color. It is noted that a process previously developed to reduce green coloration in tobacco-derived RuBisCO was not particularly effective for treating the alfalfa-derived RuBisCO samples.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method for purifying a plant-derived protein-enriched material, the method comprising:
   a) receiving a plant-derived, protein-enriched material comprising RuBisCO, F2 fraction proteins, or a combination thereof, wherein the plant-derived, protein-enriched material further comprises undesirable color;
   b) treating the plant-derived, protein-enriched material with peracetic acid to give a peracetic acid-treated mixture;
   c) washing the peracetic acid-treated mixture with water on a filter, wherein a solid treated protein-containing material is retained on the filter;
   d) solubilizing the solid treated protein-containing material to give a solution and adjusting the pH of the solution to a basic pH to give a basic solution; and
   e) processing the basic solution on a filter to afford a retentate comprising a protein concentrate or isolate having a lighter color as compared with the plant-derived, protein-enriched material.

2. The method of claim 1, wherein the undesirable color is green.

3. The method of claim 1, wherein the plant-derived, protein-enriched material comprises material from a plant comprising green leaves.

4. The method of claim 1, wherein the plant-derived, protein-enriched material comprises material from a plant selected from the group consisting of trees, bushes, grasses, ferns, vines, mosses, algae, herbs, or a combination thereof.

5. The method of claim 1, wherein the plant-derived, protein-enriched material comprises material from a plant selected from the group consisting of spinach, alfalfa, Swiss chard, kale, chicory, amaranth, barley leaves, mustard greens, clover, carrot leaves, beet leaves, and combinations thereof.

6. The method of claim 5, wherein the plant-derived, protein-enriched material comprises material from alfalfa.

7. The method of claim 1, wherein the treating step b) is conducted at a pH of 3 to 5.

8. The method of claim 1, wherein the treating step b) is conducted at a temperature of 25° C. to 42° C.

9. The method of claim 1, wherein the treating step b) comprises treating the plant-derived, protein-enriched material with peracetic acid in the form of an aqueous solution comprising at least 3% by weight peracetic acid.

10. The method of claim 1, wherein step c) comprises washing the peracetic acid-treated mixture with water on a 1.4 μm pore filter.

11. The method of claim 1, wherein step c) comprises washing the peracetic acid-treated mixture with water having a pH of less than 5.

12. The method of claim 1, wherein step d) comprises resolubilizing the solid treated protein-containing material in an aqueous solution.

13. The method of claim 1, wherein step e) comprises processing the basic solution on a 10 nm filter.

14. The method of claim 1, further comprising spray drying the protein concentrate or isolate.

15. The method of claim 1, wherein the protein concentrate or isolate comprises 60% or more RuBisCO, F2 fraction proteins, or a combination thereof by weight.

16. The method of claim 15, wherein the protein concentrate or isolate comprises 60% or more RuBisCO by weight.

17. The method of claim 15, wherein the protein concentrate or isolate comprises 70% or more RuBisCO by weight.

18. The method of claim 15, wherein the protein concentrate or isolate comprises 80% or more RuBisCO by weight.

19. The method of claim 1, further comprising incorporating the protein concentrate or isolate into a composition for human or animal consumption.

* * * * *